(12) United States Patent  
Louie (10) Patent No.: US 7,125,965 B2  
(45) Date of Patent: Oct. 24, 2006

(54) MRI PROBES OF MEMBRANE POTENTIAL

(75) Inventor: Angelique Louie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 261 days.

(21) Appl. No.: 10/700,712

(22) Filed: Nov. 3, 2003

(65) Prior Publication Data

US 2004/0230044 A1  Nov. 18, 2004

Related U.S. Application Data

(60) Provisional application No. 60/423,296, filed on Nov. 1, 2002.

(51) Int. Cl.
 C07F 5/00 (2006.01)
 G01N 24/08 (2006.01)
 A61B 5/055 (2006.01)

(52) U.S. Cl. ............... 534/16; 534/15; 424/9.363; 436/173

(58) Field of Classification Search ............ 534/15, 534/16; 424/9.363; 436/173
 See application file for complete search history.

(56) References Cited

U.S. PATENT DOCUMENTS 5,325,854 A 7/1994 Ehnholm
5,532,006 A 7/1996 Lauterbur et al.

OTHER PUBLICATIONS

Aime, S. et al. (1998) *Chemical Society Reviews* 27, pp. 19-29.
Aime, Silvio et al. (2002) *JMRI* 16, pp. 394-406.
Bancel, S. & Hu, W. (1996) *Biotech Progress* 12, pp. 398-402.
Bearse, M. & Sutter, E. (1996) *J. Opt. Soc. Am A* 13, pp. 634-640.
Cabrini, G. & verkman, A. (1986) *J. Membrane Biol.* 92, pp. 171-182.
Caravan, Peter et al. (1999) *Chem Rev* 99, pp. 2293-2352.
Chibisov, A. & Görner, H. (1998) *Chemical Physics* 237, pp. 425-442.
Damadian, R. (1971) *Science* 171, pp. 1151-1153.
DiLoreto, D. et al. (1995) *Brain Res.* 698, pp. 1-4.
Duncan, J. R. et al. (1994) *Inves. Radiol* 29, S58-S61.
Eversole-Cire, P. et al. (2000) *Inv. Opth. Vis. Sci.* 41, pp. 1953-1961.
Görner, H. & Chibisov, A. K. (1998) J. Chem Soc. Faraday. Trans. 94, pp. 2557-2564.
Hawes, N. et al. (2000) *Inv. Opth. Vis. Sci* 41, pp. 3149-3157.
Heermeier, K. et al. (1995) *Cells and Materials* 5, pp. 309-320.
Igelmund, P. et al. (1997) *Pflugers Archiv-Eur J. Physiol* 433, P293-P293 Suppl. S.
Ito, Y. et al. (1999) *Nature Biotech* 17, pp. 73-75.
Jacobs, R. E. and Fraser, S.E. (1994) *Science*, 681.
Jahangiri, A. et al. (2000) *Mol. Cell. Biochem.* 206, pp. 33-41.
Jasanada, F. et al. (1996) *Bioconj. Chem* 7, pp. 71-81.
Keene, D. et al. (2000) *Epileptic Disorders* 2, pp. 57-63.
Kimura, K. et al. (1992) *Chem. Soc. Perkin Trans* 2, pp. 613-619.
Kimura, K. et al. (2000) *Analyst* 125, p. 1091-1095.
Lauterbur, P. (1973) *Nature* 242, pp. 190-191.
Lehmann-Horn, F & Jurkat-Rott, K. (1999) *Physiol. Rev.* 79, pp. 1317-1372.
Louie, A. Y. et al. (2000) In Vivo Visualization of Gene Expression by Magnetic Resonance Imaging, *Nature Biotechnology* 18, pp. 321-325.
McWhinney, C. et al. (2000) *Mol. Cell. Biochem.* 214, pp. 111-119.
Moats, R. et al. (1997) *Angewandte Chemie-International Edition in English* 36, pp. 726-728.
Nattel, S. & Li, D. (2000) *Circulation Research* 87, pp. 440-447.
Plasek, J. & Sigler, K. (1996) *J. Photochem. Photobio.* 33, pp. 101-124.
Porteracailliau, C. et al. (1994) *PNAS* 91, pp. 974-978.
Shoji, J. et al. (1998) *Ophthalmic Res* 30, pp. 172-179.
Taylor, L. D. and Davis, R. B. (1963) *J. Org. Chem.* 28, p. 1713.
Tweedle, M. (1997) *European Radiology* 7, S225-S230.
Waggoner, A. (1976) *J. Membrane Biol.* 27, pp. 317-334.
Wojtyk, J. T. C. et al. (1998) *Chem. Commun.*, pp. 1703-1704.
Wu, J. Y. & Cohen, L. B. (1993) Fluorescent and Luminescent Probes for Biological Activity, Academic Press, San Diego, pp. 389-403.
Zhi, J. et al. (1995) *J. Photochem. Photobio A:Chem* 92, pp. 91-97.
Keene DL. et al. (2000) *Epileptic Disorders* 2, pp. 57-63.

*Primary Examiner*—Bernard Dentz
(74) *Attorney, Agent, or Firm*—Fenwick & West LLP (57) ABSTRACT

The invention provides methods and compositions for molecular resonance imaging of membrane potential. The compositions comprise an indicator moiety attached through an optional linker to a macrocycle component that binds a lanthanide. The indicator moiety changes conformation in response to alterations in membrane potential and alters the interaction of the bound lanthanide with water. This alteration produces a detectable change in MRI signal, notably the $T_1$ value. A preferred indicator moiety is spiropyran as it exhibits membrane-potential driven interconversions between the closed-ring spiropyran conformer and the extended merocyanine conformer. A preferred macrocycle is DO3A, known to bind gadolinium and an established MRI contrast agent. The methods of the invention comprise in vivo and in vitro uses of compositions of the invention to obtain MRI images that provide information about membrane potential.

27 Claims, 9 Drawing Sheets

MRI PROBES OF MEMBRANE POTENTIAL

CROSS REFERENCE TO RELATED APPLICATIONS

This application claims the benefit of U.S. Provisional Application No. 60/423,296, filed Nov. 1, 2002, the entire disclosure of which is hereby incorporated by reference in its entirety for all purposes.

STATEMENT REGARDING FEDERALLY SPONSORED RESEARCH OR DEVELOPMENT

The U.S. Government has certain rights in this invention pursuant to Grant No. 1 R03 EY 13941 awarded by the National Eye Institute.

BACKGROUND OF THE INVENTION

1. Field of the Invention

The invention relates to methods and compositions useful for magnetic resonance imaging (MRI) of membrane potential.

2. Description of the Related Art

Magnetic resonance imaging (MRI) contrast agents are known in the art and are used to improve contrast amongst various soft tissues. Conventional magnetic resonance contrast agents interact with water to alter the signal from water protons that provide the image. Such contrast agents, however, are insensitive to membrane potential. Consequently, magnetic resonance imaging, while providing excellent spatial resolution in images of biologic structures, provides little or no information about the electrical activity of the imaged tissues. For electrically-excitable tissues such as neurons, and muscles it would be advantageous to obtain molecular resonance based images of membrane potential from which tissue function could be assessed in a non-invasive manner.

U.S. Pat. No. 5,325,854 to Enholm titled "Magnetic Resonance Imaging" provides ionic or ionizable paramagnetic substances capable of associating with cell membrane lipids to provide a contrast agent that has an electron spin resonance (ESR) signature. The association of the ESR component with the membrane changes the ESR signature. These substances can be used with a modification of molecular resonance imaging known as electron spin resonance enhanced magnetic resonance imaging (ESREMRI) to image biological electromagnetic activity, but cannot be used with conventional MRI equipment.

U.S. Pat. No. 5,532,006 to Lauterbur et al. titled "Magnetic Gels Which Change Volume in Response to Voltage Changes for MRI" relies on electric-field induced volume changes of a matrix in which is distributed a superparamagnetic component. Changes in the specific volume of the matrix affect the response of the distributed component to the magnetic field and so provide a basis for imaging membrane potential. The requirement in that the compositions be a matrix, however, may limit the ability to safely administer the disclosed compositions or to have them partition readily out of the vasculature into other tissue compartments.

Thus there is a need in the art for contrast agents that act as MRI probes of membrane potential that can be used with conventional MRI equipment and that do not rely changes in matrix volume to produce a signal. The present invention provides for these and other advantages over the prior art.

SUMMARY OF THE INVENTION

The present invention is defined by the following claims, and nothing in this section should be taken as a limitation on those claims. Disclosed herein are compounds and compositions useful as molecular resonance image probes of membrane potential.

Accordingly one aspect of the invention is a composition comprising an indicator moiety capable of adopting at least two conformations, wherein the equilibrium between said at least two conformations is altered by a membrane potential, and wherein said indicator moiety is bound through an optional linker group to a macrocycle within which a lanthanide atom is chelated. The interaction of the chelated lanthanide atom with water is altered by a change in the equilibrium between said at least two conformers of said indicator moiety. In one aspect, the composition has a structure shown in FIG. 2, where $R_1$ is selected from $C_nH_{2n+2}$, $C_nH_{2n}$ or a combination of both, where n is 0 to 4, inclusive, and where $R_2$–$R_7$ are independently selected from H, $CH_3$, phenyl, or a bulky steric-hindering group including, e.g., a substituted benzyl moiety such as a nitrosobenzyl group, or pyrimidine, or another planar ring-type group, and where $A^-$ is independently selected from $COO^-$, $PO_3^{2-}$, or another other lanthanide—coordinating group. In another aspect, the invention includes compositions comprising a compound of the invention and a pharmaceutically acceptable excipient. In yet another aspect, the invention includes using a compound or composition of the invention to generate a molecular resonance images of membrane potential. In addition, the invention includes methods to test compounds or compositions for their suitability as molecular resonance image probes of membrane potential. Both methods have as common steps contacting a cell with a compound or composition of the invention, and generating a molecular resonance image of the cell. In the former methods, the image includes information about the membrane potential of the imaged cell. In the latter method, the image is analyzed to determine whether it contains information about the membrane potential of the imaged cell.

BRIEF DESCRIPTION OF THE SEVERAL VIEWS OF THE DRAWING

These and other features, aspects, and advantages of the present invention will become better understood with regard to the following description, and accompanying drawings, where.

DETAILED DESCRIPTION OF THE PREFERRED EMBODIMENTS

Advantages and Utility

Briefly, and as described in more detail below, described herein are compositions useful as MRI probes of membrane potential. The compositions comprise an indicator moiety that changes conformation in response to an electric field, linked to a macrocycle component capable of binding to a paramagnetic species commonly used in MRI contrast agents.

Several features of the current approach should be noted. First, the compositions of the present invention act as MRI probes of membrane potential because changes in the conformation of the indicator moiety affect the access of water protons to the paramagnetic species bound by the macrocycle component. Second, the compositions of the invention are useful as MRI probes of membrane potential when used to image cultured cells such as, e.g., cultured neurons, myoblasts, myofibrils, or to image isolated organs or sections thereof such as, e.g., brain, ganglia, spinal cord, retina, heart and other muscles.

Advantages of this approach are numerous. The invention provides for the use of MRI to carry out non-invasive monitoring of membrane potential. Thus, the invention provides all of the advantages of contrast-enhanced MRI including, e.g., enhanced safety as compared to use of ionizing radiation for imaging, high spatial resolution, while providing information about the membrane potential of the imaged tissues.

The invention is useful for, e.g., diagnosing and assessing the functional state of tissues, especially those that are electrically excitable, and for screening the effects of drugs on tissues that can be functionally evaluated on the basis of membrane potential. It permits early diagnosis, prior to the appearance of functional impairment of retinal disease such as age-related macular degeneration, allowing earlier treatment and prevention of blindness. In addition, the invention can be used to simultaneously image myocardial electrical activity and contractility, providing advantages to the study of cardiac normal and pathophysiology beyond what can be determined from monitoring electrical activity alone as by, e.g., EKG recordings.

Definitions and Abbreviations

Terms used in the claims and specification are defined as set forth below unless otherwise specified.

The term "ameliorating" refers to any therapeutically beneficial result in the treatment of a disease state, e.g., a neurological or electrophysiological disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to assess membrane potential using MRI.

An indicator moiety is a molecule that undergoes a conformational change in response to membrane potential changes. As a result of that conformational change, the indicator moiety effects an alteration of the interaction of an associated macrocycle-chelated lanthanide and water.

It must be noted that, as used in the specification and the appended claims, the singular forms "a," "an" and "the" include plural referents unless the context clearly dictates otherwise.

"La" is used throughout the specification and claims to indicate a Lanthanide.

Recited ranges are inclusive of the limits unless otherwise indicated. Recited amounts, temperatures, etc. have been disclosed with care, but are intended to encompass variations on the order of ±20% to allow for normal experimental error and deviation, except where otherwise indicated.

Introduction

Since its inception in the early 1970's magnetic resonance imaging (MRI) has come to occupy a prominent place in medical diagnostics. MRI excels as a noninvasive method to three-dimensionally image deep tissues in living subjects but gives little information about biochemical processes. Gradual improvements in the design of image acquisition protocols and hardware have lead to the ability to probe structures in vivo at cellular resolution (10 µm). Recent advances in contrast agent development hold the promise that MR contrast agents can be designed to be indicators of biological processes. Much as fluorescent probes opened a window to biochemistry for optical imaging techniques, one envisions that MR contrast agents will fulfill the same role for MRI.

Depolarization of membranes is an integral component of many signal transduction cascades. Abnormal changes at this level of signaling can be symptomatic of pathological conditions. In epilepsy, for example, there are changes in the pattern of nerve activity in the brain preceding and following seizures. In cardiovascular systems irregular electrical activity can indicate underlying disease states. In the visual system, lack of activity in the retina indicates dysfunction in the detection of light. The ability to generate MR images of membrane potential therefore is of use in many fields.

Elements of MR Image Formation

Certain atomic nuclei possess a non-zero spin, which gives rise to a net magnetic moment. The nuclear magnetic moments of water protons (hydrogen atoms) supply the signal in most MR imaging experiments. The sample to be imaged is placed in a strong static magnetic field that induces the sample to become slightly magnetized with a net magnetic moment in the direction of the applied field, with an energy (angular momentum) proportional to the applied field. To encode spatial information, other fields are applied as gradients along one or more orthogonal axes. Each position in space is uniquely encoded by the energy or phase of the spins there. A radio frequency field is pulsed through the sample and the energy absorbed results in a reorientation of the net nuclear magnetization in a new direction (typically a pulse is applied to tilt the magnetization 90 degrees). After this perturbation, net energy loss by a variety of processes returns the net magnetization to its initial equilibrium orientation. The formation of an image from this process has a complicated dependence on a large number of factors.

In a typical experiment, one modifies the imaging parameters to reduce the contributions from many of these factors. In the most typical MRI experiments, signal intensity is primarily derived from proton concentration and relaxation times. Relaxation times characterize the return of net magnetization to equilibrium. It is the difference in signal intensities between spatial regions that provides contrast. Proton concentration can vary by a large percentage between soft tissue and bone, providing sharp contrast. Differences in proton density between soft tissues is more subtle, however, and contrast more likely is derived from tissue-dependent differences in relaxation times, which depend strongly on local environment.

Contrast Enhancement

The need to differentiate tissues or organs that are magnetically similar but histologically distinct has been a major impetus for the development of contrast enhancement agents. They are called contrast agents because signal is increased in their presence, thus improving contrast between that tissue and surrounding tissues. More than 30% of all clinical MR exams now employ contrast agents. However, current clinical MRI agents are not sensitive to biochemical events in cells or organs—rather, being always active they enhance the signal wherever they are present. Distinguishing tissues relies on differential distribution of contrast agents between tissues, which does not always occur. Contrast agents that are responsive to microenvironmental differences between tissues would allow discrimination based on biochemical events, extending the potential applications for MRI beyond simple anatomy.

Paramagnetic elements, such as lanthanides, make effective contrast agents. Unpaired electrons in the paramagnetic ions interact directly with surrounding water protons to dramatically reduce their relaxation times. This change in the relaxation times translates to enhanced signal. The effects of contrast agents are generally reported in terms of relaxation rates or relaxivity of the water protons, which are inversely related to the relaxation times and reflect the overall contributions of all relaxation mechanisms at work in the system. Water access to the paramagnetic ions is important for the effect (first sphere coordination).

The principles and practice of MRI image formation with and without contrast enhancement are well known to those of skill in the art and are discussed in greater detail in Aime, et al., *JMRI* 16:394–406 (2002); Caravan, et al., *Chem Rev* 99:2293–2352 (1999), and Gadian, *NMR and its Applications to Living Systems*, 2$^{nd}$ Edition, Oxford Science Publications (1995), the entire disclosures of which are incorporated by reference in their entirety for all purposes.

Measurement of Membrane Potentials

In very large cells, such as squid giant axons, one can insert an electrode into the cell and measure the potential across the membrane directly. For systems in which even microelectrodes would be too large, however, other means must be employed. Optical techniques to measure membrane potential were first suggested in 1968 based on the discovery that changes in membrane potential may be accompanied by innate optical changes (for some systems). Wu, J. Y. & Cohen, L. B. (1993) in *Fluorescent and Luminescent Probes for Biological Activity* (Academic Press, San Diego), pp. 389–403. Around the same time, it was found that stimulus-dependent changes were observed in the fluorescence of stained axons. This prompted a hunt for other dyes that show varying signal in response to membrane potential. Today, exogenous dyes for measurement of membrane potential are a large and well-studied group of indicators. These are divided into two major classes: fast (ms) and slow (s), according to the speed of their response to electrical activity. Waggoner, A. (1976) *J Membrane Biol*. 27, 317–334. Dyes have been found that experience optical changes of three types: absorbance, birefringence and fluorescence. Among the fast dyes, spiropyran is particularly interesting because it experiences a significant structural rearrangement in response to changes in membrane potential, resulting in a redistribution of charge.

Figure 1:
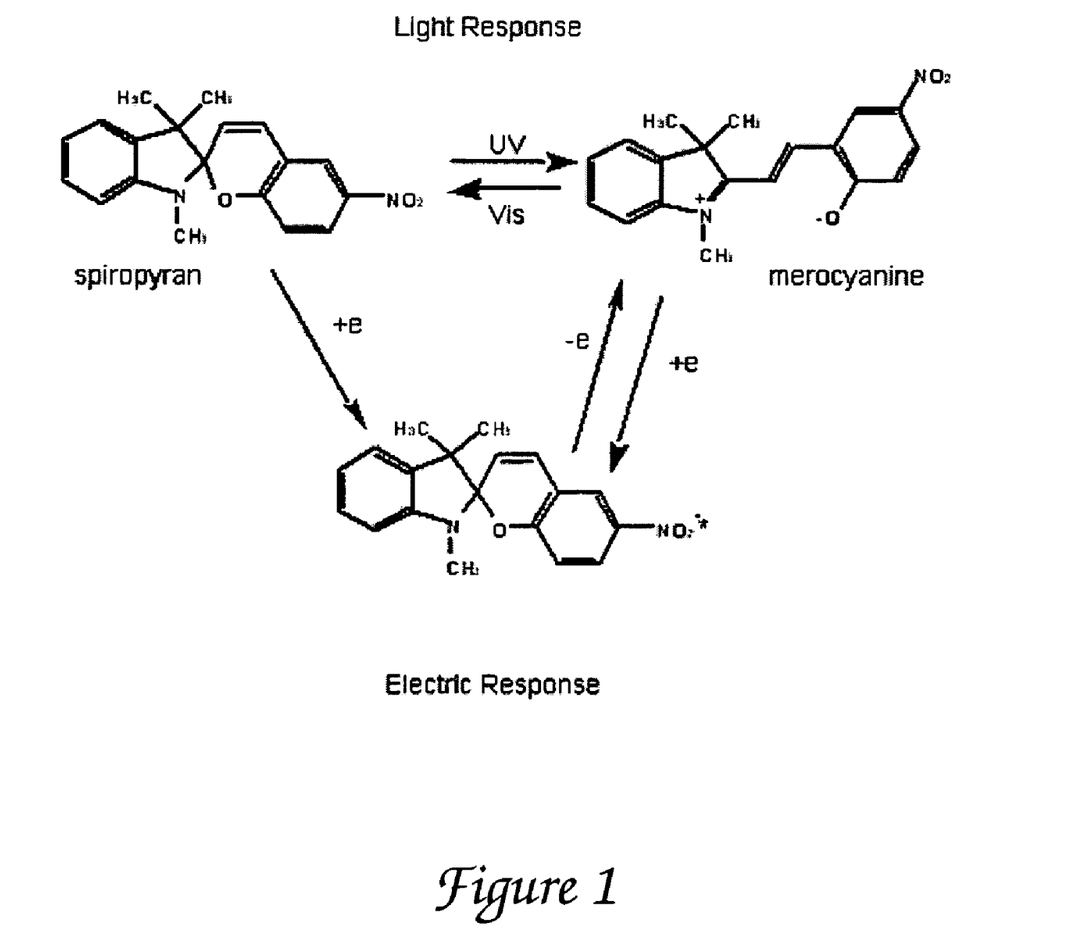
FIG. 1 illustrates the photo- or electrochemical-isomerization between spiropyran and merocyanine forms of an optical probe of membrane potential.

The dye molecule is believed to respond to membrane potentials by temporarily associating with the resting membrane in its neutral spiropyran form (FIG. 1, upper left), and releasing from the membrane when isomerized, in response to membrane hyperpolarization, to its charged merocyanine counterpart (FIG. 1, upper right). The merocyanine form of the molecule has absorbance in the visible range of light while the spiropyran form does not. Change in membrane potential results in a measurable absorbance of light by the dye. This electrochromic behavior is associated with a redox process for the nitro group ($NO_2$). Zhi, J., Baba, R., Hashimoto, K. & Fujishima, A. (1995) *J. Photochem. Photobio. A. Chem* 92, 91–97.

Interestingly, this transformation can also be triggered by illumination with light. FIG. 1 illustrates the structural changes occurring during this redox reaction and how they can be produced by response to light or to electrical activity. The merocyanine form also thermally relaxes to the closed-ring spiropyran isomer at a temperature-dependent rate.

We use spiropyran/merocyanine groups to modulate the interaction of contrast agents with membranes, and control the relaxivity properties of the contrast agents. We show that spiropyran groups, in their merocyanine form, can be engineered to shield the paramagnetic metal center of a contrast agent from water protons and that this shielding alters the contrast enhancement properties of the contrast agent in a reversible manner.

Design of the Contrast Agents

Figure 2:
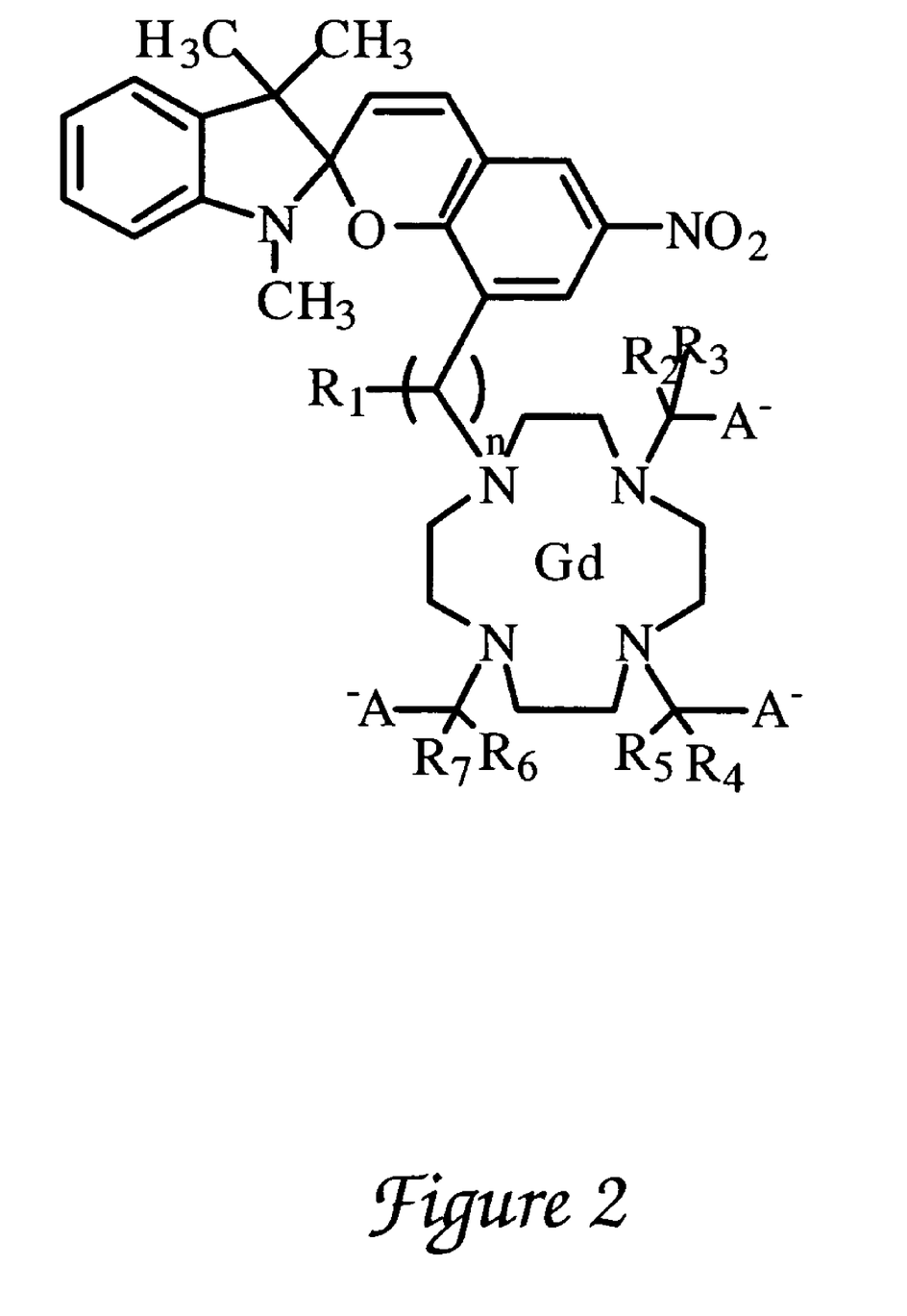
FIG. 2 is a generic structure of preferred compounds of the invention.

In one embodiment of the compounds of the invention, couple a spiropyran moiety via a linker to a macrocycle-based lanthanide chelator. The generic molecule is shown in FIG. 2 with Gd as an exemplary lanthanide.

Compounds of the Invention

In preferred embodiments, the linker length, n, is between 0 and 4 and preferably $R_1=C_nH_{2n+2}$, $C_nH_{2n}$ or a combination of both. As one of ordinary skill will recognize, synthesizing the alternate preferred embodiments may be accomplished by straightforward reactant substitutions in the reaction scheme shown in FIG. 4. For example, altering the length and character of the $R_1$ substituent can be done by substituting choromethyl methyl ether (n=1) at step one of the synthesis with chloroethyl methyl ether (n=2), or chloromethylene derivatives (to generate unsaturated versions of the linker), etc. $R_2$–$R_7$ are independently selected from H, $CH_3$, phenyl, or bulky steric-hindering groups, such as, e.g., substituted benzyl moieties (e.g., nitrosobenzyl), pyrimidine, or other planar ring type groups. Reagent substitutions for altering $R_2$–$R_7$ include, e.g., substitution of bromoacetic acid (R=H) at step four of the synthesis with 2-bromo-2-methylpropionic acid (R=$CH_3$); 2-bromo-3-methylbutyric acid (R=$CH_2(CH_3)_2$); 2-bromohexanoic acid (R=$(CH_2)_3CH_3$); 2-bromophenylacetic acid (R=phenyl); 2-bromo (myristic, proprionoic, octanoic, tetradecanoic etc) acid (R=long chain alkyl), etc. A is independently selected from $COO^{31}$, $PO_3^{2-}$, or other lanthanide—coordinating group.

Reagent substitutions for altering A include, e.g., substitution of cyclen at step four of the synthesis with cyclen containing phosphonomethyl groups in the amino functions in three positions (phosphonomethyl groups introduced by condensation of cyclen with formaldehyde and phosphorous acid or by treatment of formyl cyclen with triethyl phosphite and paraformaldehyde). Similarly, substitutions may be made by one of ordinary skill in the art for the indicator moiety. For the exemplified spirobenzopyran, alternates such as spirobenzothiopyran and other substitutions may be made without departing from the scope of the invention. For the molecule described in the Examples, below, $A=COO^{31}$, $R_1=C_nH_{2n+2}$, n=2, and $R_2$–$R_7$ are each H.

We show that the merocyanine form of the spiropyran moiety prevents the chelated lanthanide ion from interacting with water. This is consistent with a number of observations from the literature. The merocyanine form is known to bind metals, the spiropyran form does not. Chibisov, A. & Görner, H. (1998) *Chemical Physics* 237, 425–442; Görner, H. & Chibisov, A. K. (1998) *J. Chem. Soc. Faraday. Trans*. 94, 2557–2564; Wojtyk, J. T. C., Kazmaier, P. M. & Buncel, E. (1998) *Chem. Commun*., 1703–1704. Metal complexation is favored by 6-nitro, 8-methoxy-substituted spiropyran derivatives and this complexation stabilizes the merocyanine from thermal decay back to the spiropyran form. The lifetime for uncomplexed merocyanine is on the order of 12–60 seconds (25 s for the merocyanine shown in FIG. 1). Görner, H. & Chibisov, A. K. (1998). In the presence of metal this lifetime increases significantly. The increase in merocyanine lifetime is strongly dependent on the type and concentration of metal. For example, in the presence of 0.15 mM Pb(II) the lifetime for merocyanine is 300 sec. In 1 mM Pb(II) the lifetime increases to 600 sec. Binding of lanthanides such as europium and terbium at 0.15 mM results in lifetimes on the order of 300 seconds. The merocyanine form is still readily converted back to spiropyran by visible light irradiation.

Figure 3:
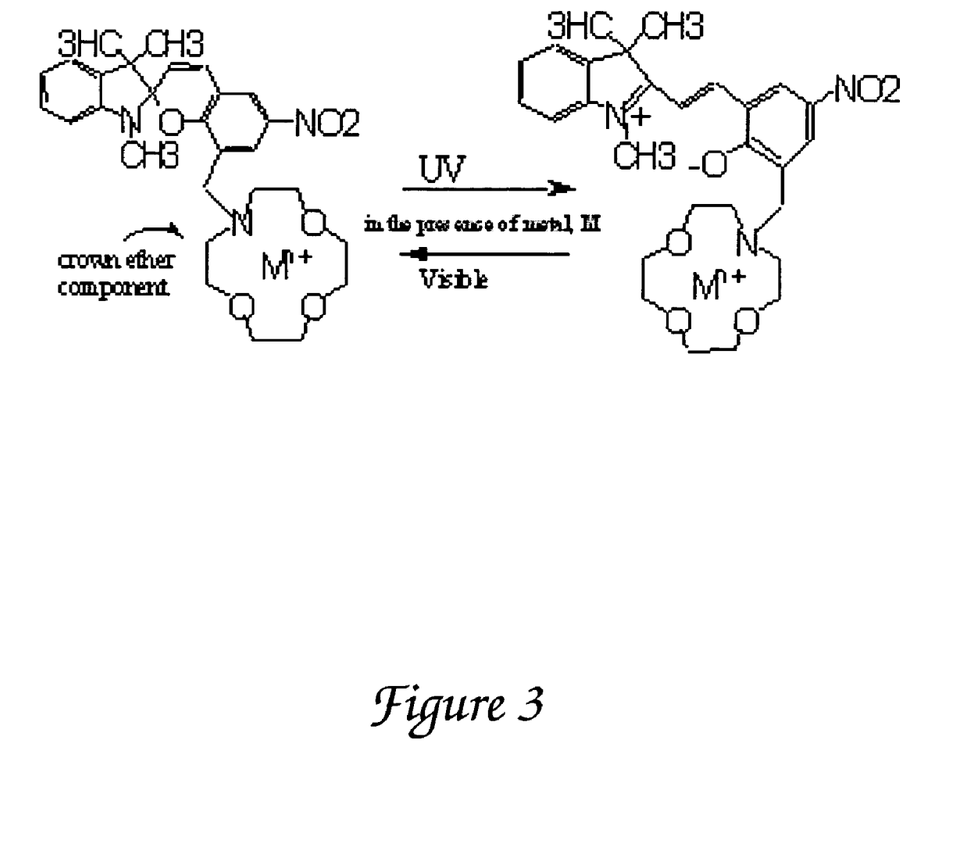
FIG. 3 illustrates the interaction of a spiropyran crown ether derivative with metals.

Reports in the literature on crown ether conjugates with spiropyran indicate that the presence of a monoazacrown moiety enhances merocyanine's interaction with metals. The merocyanine group interacts with metals bound by crown ethers while the spiropyran form does not. Kimura, K., Yamashita, T. & Yokoyama, M. (1992) *Chem. Soc. Perkin Trans* 2, 613–619. Multinuclear NMR spectrometry indicates that the metal ion in the crown ether moiety interacts strongly with the phenolate anion of merocyanine. Kimura, K., Sakamoto, H., Kado, S., Arakawa, R. & Yokoyama, M. (2000) *Analyst* 125, 1091–1095. The interaction of a spiropyran crown ether derivative with metals is illustrated in FIG. 3. The derivatized crown ethers show a higher affinity for multivalent metal ions than to monovalent metal ions. In spite of this metal binding, visible light irradiation triggers immediate isomerization back to the spiropyran form. Syntheses of several monoazacrown conjugates are described by Kimura et. al. (2000) and provide the basis for the synthesis we describe below. We modified this synthesis by substituting a macrocycle known to bind Gd, e.g. DO3A (macrocycle component shown below linker moiety in the FIG. 2), for the crown ether. The macrocycle component chelates the lanthanide gadolinium and the resulting metal complex acts as a contrast agent. Although crown ethers behave differently from cyclens (the four nitrogen macrocycle component of FIG. 2), we have shown that this synthesis can be accomplished reasonably. The synthesis is given in FIG. 4, and is described in detail in Example 1, below.

Figure 5:
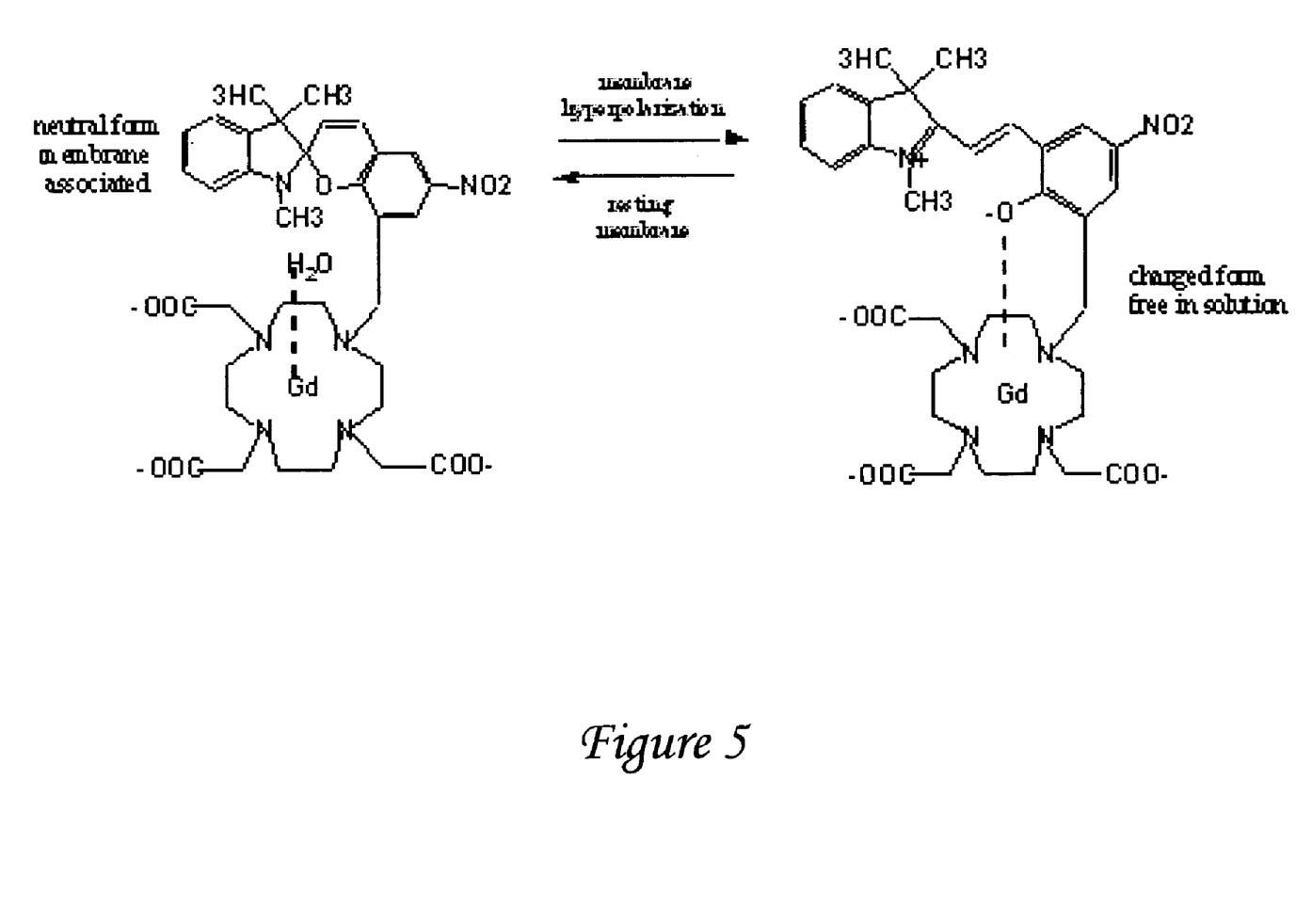
FIG. 5 illustrates mechanisms by which spiropyran interconversions modulate access of water to chelated lanthanide.

The ability of this agent to create contrast in an MRI image depends on the interaction of water with the lanthanide such as europium, terbium or gadolinium. Interaction of the phenolate anion of the merocyanine group with a lanthanide such as gadolinium occupies a coordination site on the gadolinium and thus, limits interaction with water (FIG. 5). This interaction occurs between a DO3A-chelated lanthanide such as Gd and the phenolate anion in the compounds of the invention. In this configuration the contrast agent does not enhance the MR image. When membrane potential changes to reverse the merocyanine form back to the spiropyran form, coordination to the lanthanide is lost so water is again free to occupy that site, activating the contrast agent.

Without wishing to be bound by theory, while we believe the dominant mechanism affecting efficacy of the contrast agent is the interaction between the merocyanine component and the metal, we see the potential for another mechanism to affect contrast. The spiropyran isoform is membrane-associated while the merocyanine form is free in aqueous solution, and so the spiropyran-derivatized contrast agent also likely associates with membranes. When membrane-localized, the DO3A component may experience a different water environment than in the aqueous compartment and these changes in interaction with water can affect the MRI signal. Membrane-associated contrast agent, with limited water access, therefore can show reduced enhancement of the MR image, compared to the contrast agent when free in solution. Based on the structures of the compounds of the invention, these effects may be minor.

Methods of the Invention

Methods of the invention comprise administering or applying a sufficient amount of a compound of the invention in vivo or in situ and obtaining one or more contrast-enhanced MRI images, wherein the contrast is an indication of membrane potential. Methods of the invention further comprise assaying the activity of compounds of the invention in in vivo or in vitro tests to characterize the compounds of the invention.

Pharmaceutical Compositions of the Invention

Methods for diagnosing, characterizing the severity of, and staging diseases that are caused or accompanied by disturbances in the normal electrophysiological activity of excitable cells also are encompassed by the present invention. Said methods of the invention include administering a sufficient amount effective amount of a compound of the invention. The compounds of the invention can be formulated in pharmaceutical compositions for in vivo administration, preferably to a mammal, more preferably to a human. These compositions can comprise, in addition to one or more of the compounds of the invention, a pharmaceutically acceptable excipient, carrier, buffer, stabiliser or other materials well known to those skilled in the art. Such materials should be non-toxic and should not interfere with the function of the active compound. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

The actual amount administered, and rate and time-course of administration, will depend on the nature of the compound, as well as the target area to be imaged. Prescription of treatment, e.g. decisions on contrast agent dosage etc, is within the responsibility of radiologists and other medical doctors, and typically takes account of the disorder to be imaged, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of synthetic organic chemistry, biochemistry, and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

Example 1

Synthesis and Characterization of an MRI Probe of Membrane Potential

Figure 4:
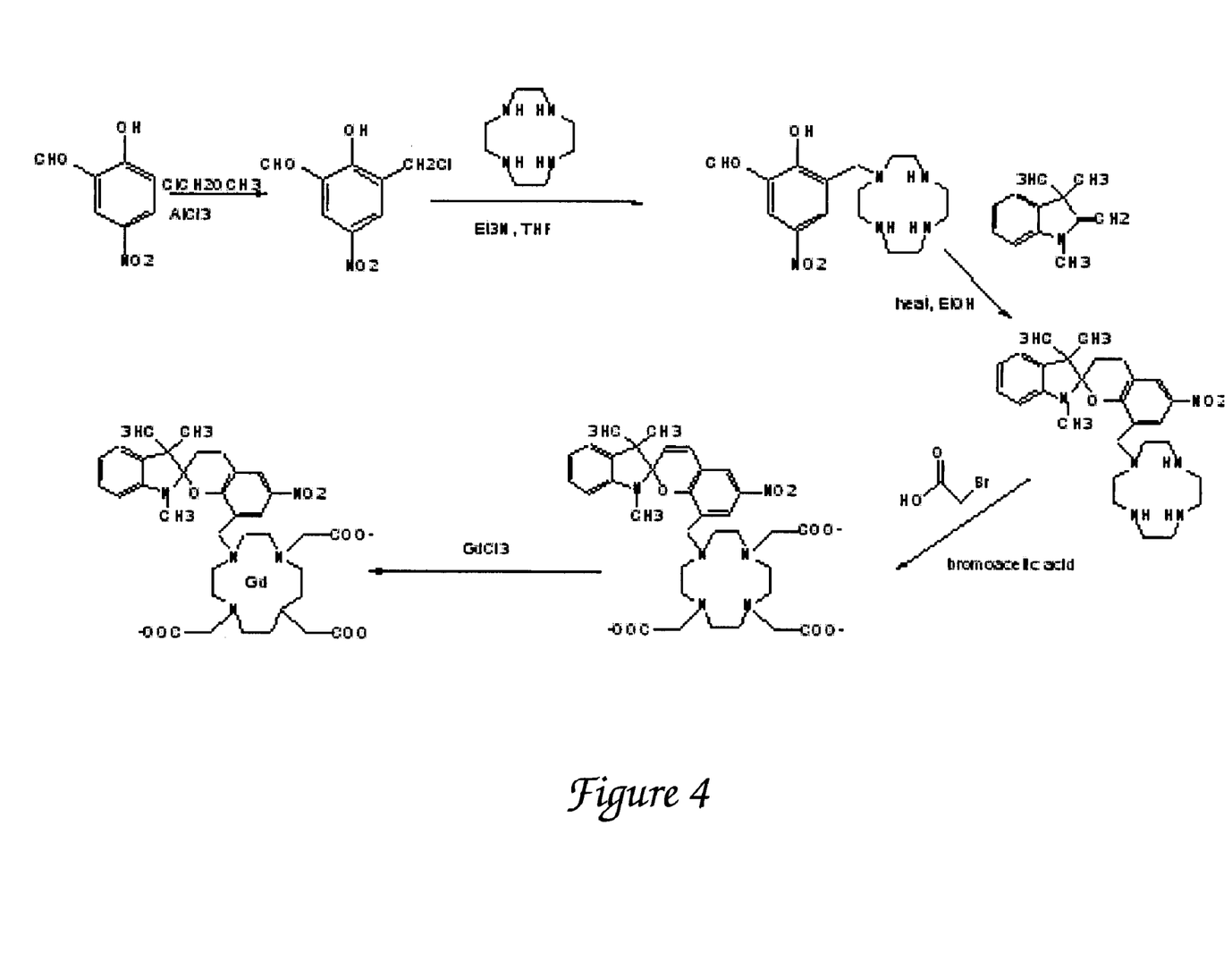
FIG. 4 illustrates the synthetic scheme for preferred compounds of the invention.
Figure 6:
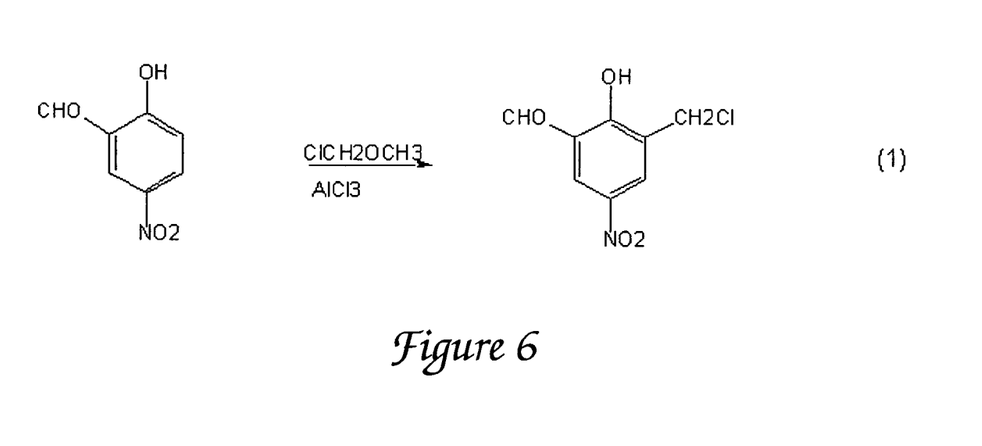
FIG. 6 is a detail of step one of the synthetic scheme illustrated in FIG. 4.

A compound having the structure shown as the final product in the scheme detailed in FIG. 4 was synthesized and characterized. Reaction step (1) (shown in isolation in FIG. 6) proceeds well and the product was characterized by $^1$H NMR spectroscopy (peak obtained at MW=214). This product was readily purified by recrystallization from hot n-hexane. The yield of this reaction in our hands was not established. The literature value is 89% isolated yield. L. D. Taylor and R. B. Davis, *J. Org. Chem.* 1963, 28, 1713.

Figure 7:
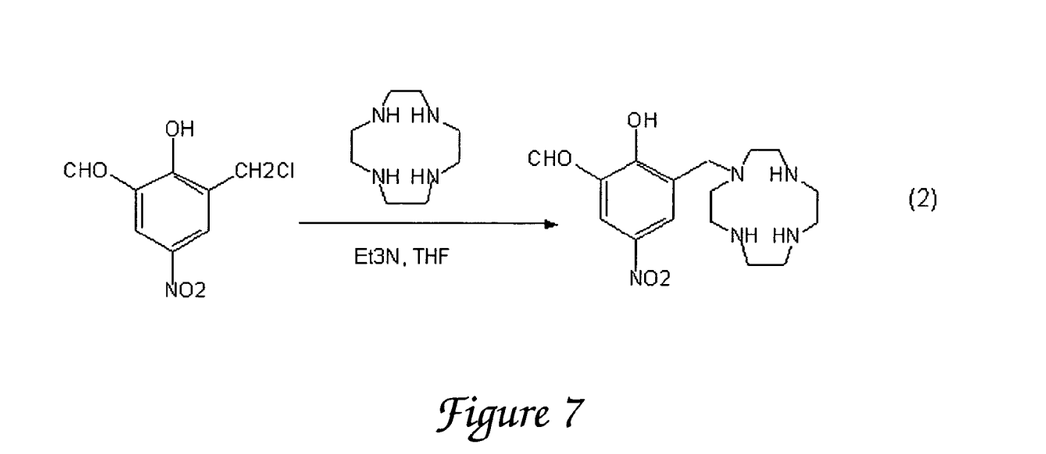
FIG. 7 is a detail of step two of the synthetic scheme illustrated in FIG. 4.
Figure 8:
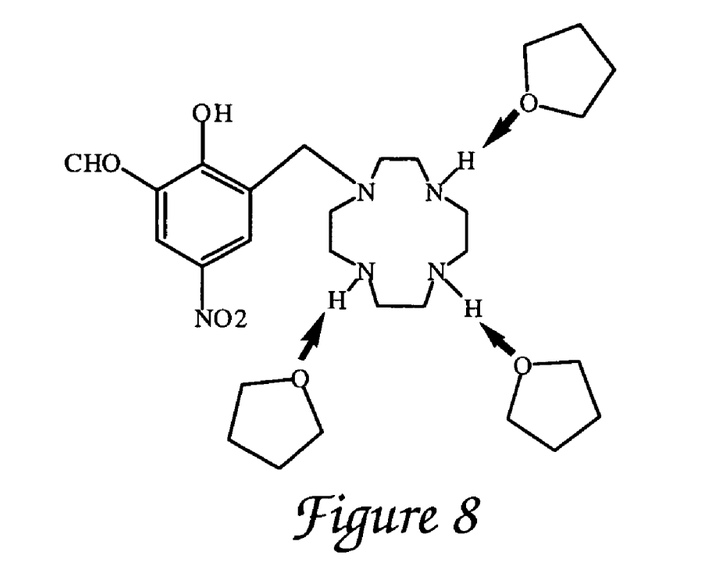
FIG. 8 is a proposed crystal structure of the product of step two in the reaction scheme shown in FIG. 4 and detailed in FIG. 7.

Reaction step (2) (shown in isolation in FIG. 7) also proceeded and the crude product was purified by recrystallization from ethanol/tetrahydrofuran. Small, square-shaped orange crystals were obtained over a period of two days in ca. 12% yield. Analysis of these crystals via $^1$H NMR spectroscopy suggests that their crystal structure may contain tetrahydrofuran (see FIG. 8). Mass spectroscopy yielded an m/z peak at 352. Further addition of tetrahydrofuran to the ethanol mixture yielded a second crop of similar crystals. However, this second crop was coated in orange-colored viscous oil, characteristic of material that had come out of solution too quickly. This material is to be further recrystallized to improve product yield.

Figure 9:
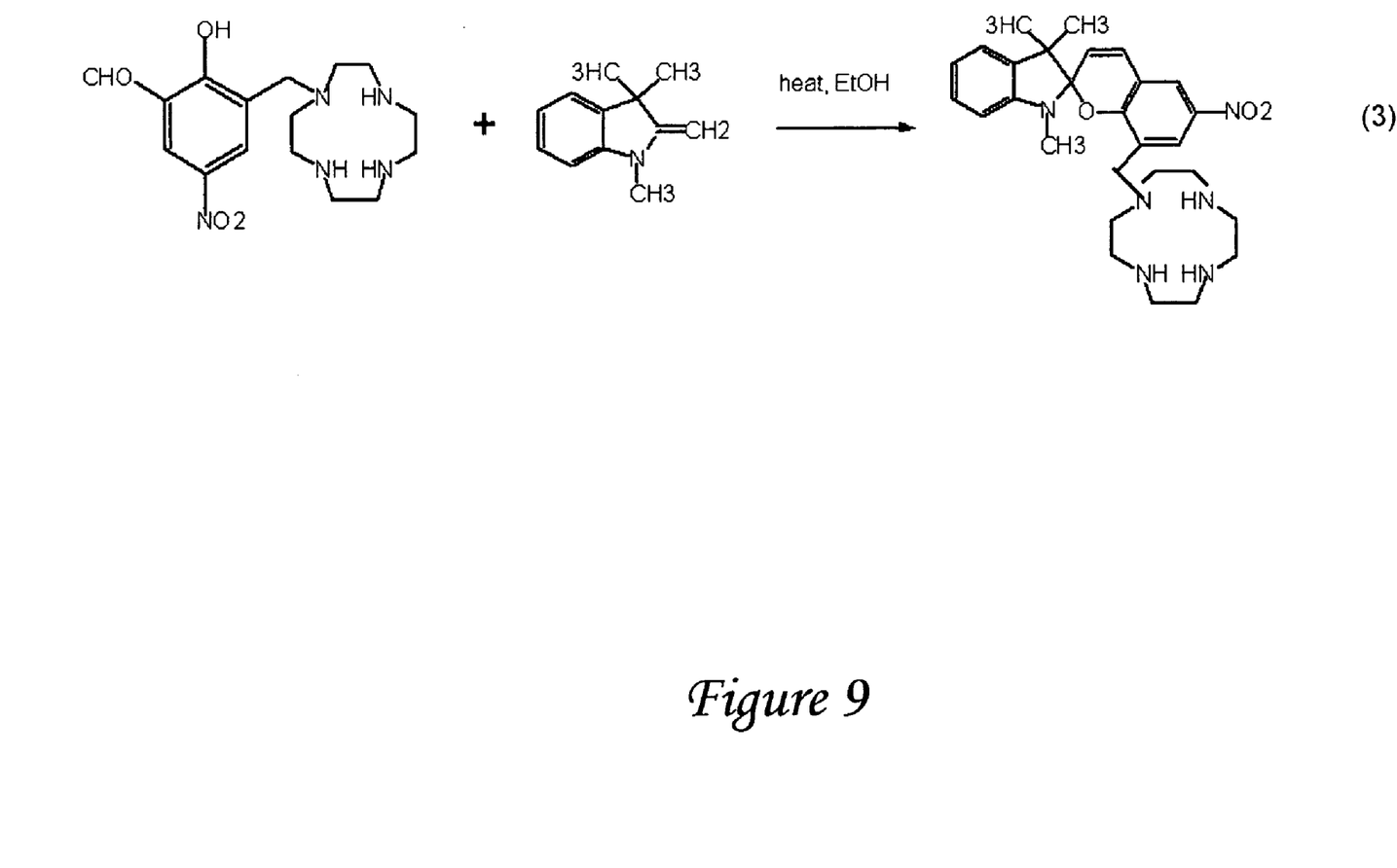
FIG. 9 is a detail of step three of the synthetic scheme illustrated in FIG. 4.

Reaction step (3) (shown in isolation in FIG. 9) was carried out under reflux (approximately 80° C.) proceeded well and yielded a solid product as expected. Previous attempts to synthesize this compound have yielded viscous oil. Purification of the product from reaction (2) appears to lead to a purer product from reaction (3) as we obtained a solid instead of an oil. This product was analyzed by $^1$H NMR and by ES mass spectral analysis: FW ca. 506, [M]+504 (100%).

Figure 10:
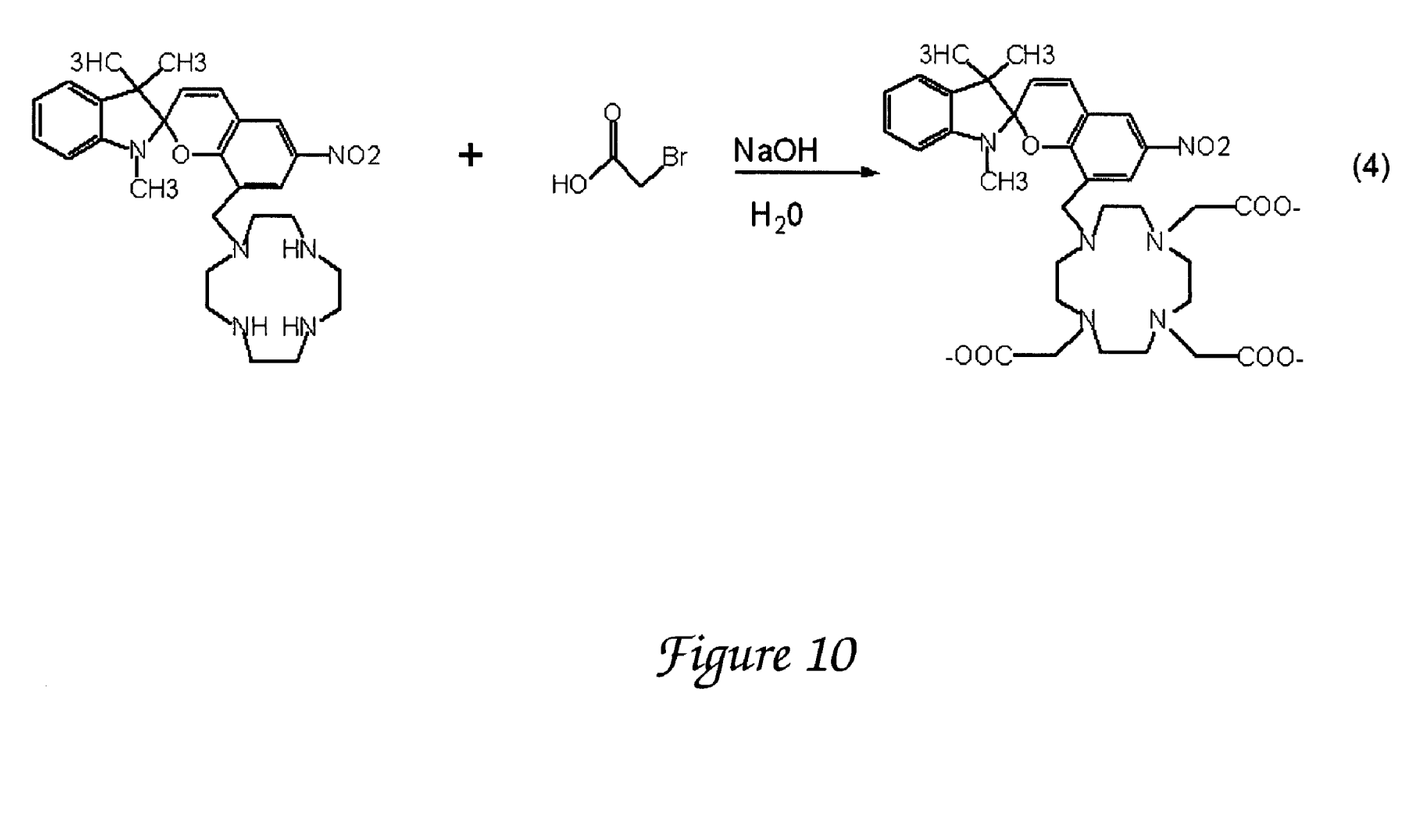
FIG. 10 is a detail of step four of the synthetic scheme illustrated in FIG. 4.

Reaction step (4) (shown in isolation in FIG. 10) was conducted overnight at pH=10–11. However, the pH dropped to a value of 9 after 24 h. Thus, the pH was again raised to a value of ca. 10 and allowed to react for a further 24 h, during which time the reaction mixture maintained its pH value of ca. 10. It appears that at least 48 hours are necessary for the reaction to go to completion as indicated by the lack of further pH change. ES mass spectral analysis indicated a prominent peak at 701 (expected mass of the ligand+Na$^+$).

Reaction step 5 (i.e., the final reaction step shown in FIG. 4) involves the insertion of the metal to the macrocycle. The sample was run through a Chelex 100 column after first neutralizing the reaction mixture to pH=7. However, upon eluting with water, only pale yellow oil was obtained. This did not display the characteristic absorbances of ca. 510 and 550 nm upon exposure to UV-light irradiation. In addition, it was observed that a band of purple-colored material was trapped at the top of the Chelex column. Various solvents were used to try to pass this band through the column, and ethanol and chloroform each were found to be effective to elute the product. This purple-colored material displayed characteristic color changes expected for the final product. UV irradiation (described in the following example) produced a product with absorbances at ca. 510 and 550 nm. Irradiation with white light eliminates these absorbance peaks. Mass spec for the product from step 5 yielded a peak at 835 and also peak at 678 (representing either free ligand or artifactual dissociation of product during electrospray).

Example 2

Irradiation of Spirobenzopyran-DO3A Compound

Figure 11:
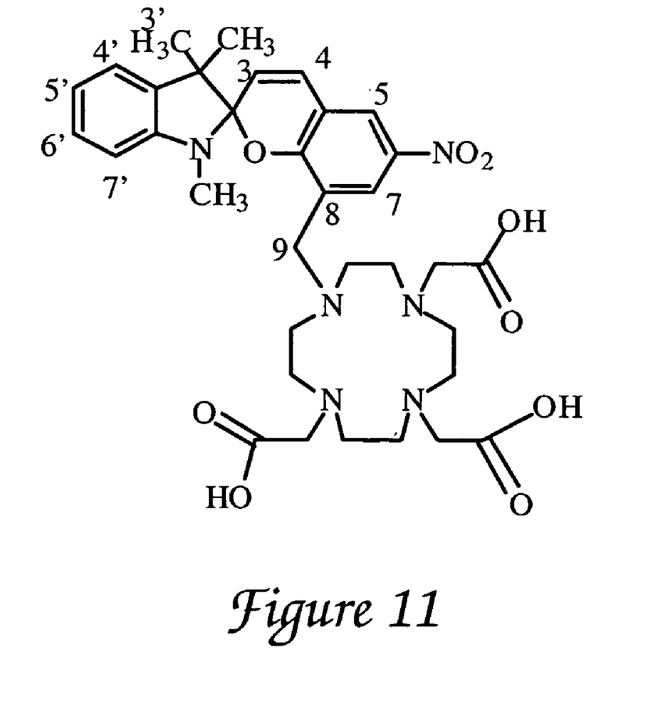
FIG. 11 shows NMR proton assignments of the product of the synthetic scheme illustrated in FIG. 4.

A 5 mm NMR tube was charged with a solution of the spirobenzopyran-DO3A compound (ca. 0.03 g) in 0.5 mL of DMSO-d6. A purple-colored solution resulted. Exposing this sample to white-light (10 W quartz halogen lamp) for 2 min led to a color change to give a pale yellow solution. The $^1$H NMR spectrum of this yellow-colored solution indicated that both the spirobenzopyran-DO3A and the merocyanine-DO3A isomers were present in solution in approximately equal concentrations. To further bias the mixture to one isomer in solution, namely the spirobenzopyran-DO3A isomer, the same sample was irradiated with white light for an additional 4 h. Upon re-running the $^1$H NMR spectrum of this sample it was clear that numerous peaks had decreased in intensity while some other peaks had grown in intensity. Analysis of this spectrum allowed the full characterization of the spirobenzopyran-DO3A isomer. The NMR data are as follows: 1H-NMR (300 MHz, DMSO-Δ6): d1.20 (s, 3', 3H), 1.24 (s, 3', 3H), 2.63 (s, NCH3, 3H), 3.35 (m, DO3A, 22H), 4.21 (s, 9, 1H), 4.22 (s, 9, 1H), 6.00 (d, 3, J=10.5 Hz, 1H), 6.63 (d, 7', J=7.8 Hz, 1H), 6.82 (t, 5', J=7.8 Hz, 1H), 7.00 (d, 4', J=7.8 Hz, 1H), 7.04 (t, 6', J=7.8 Hz, 1H), 7.23 (d, J=10.5 Hz), 1H), 8.11 (d, 5, J=2.7 Hz, 1H), 8.14 (d, 7, J=2.7 Hz, 1H). FIG. 11 shows the proton assignments derived from the NMR spectrum.

Example 3

Relaxation Analysis of Spirobenzopyran-DO3A Compound

A 30 ml spherical bulb containing a 0.84 mM aqueous solution of the spirobenzopyran-Gd3+(DOTA) complex was inserted into a 5 mm NMR tube containing 0.3 mL of $D_2O$. The sample was subjected to UV-irradiation using an 8W handheld lamp for 15 h then its $T_1$ value measured using standard inversion-recovery methods. A $T_1$ value of 2.703 was obtained. The sample was then irradiated with white light for 15 h and its $T_1$ re-evaluated and a $T_1$ of 2.652 was obtained. Larger $T_1$ differences are expected to result from the use of more intense irradiation.

Example 4

In vitro Characterization of Compounds of the Invention

The ability of the compounds of the invention to respond to membrane potentials and enhance MRI contrast is initially tested in vitro. Because the spiropyran-merocyanine transition can be triggered by light irradiation, the first steps of characterization can be simplified by using light as a stimulus for testing the compounds isomerization properties, rather than membrane potential. Absorbance spectra for the contrast agents are measured after UV or visible light irradiation to confirm that the spiropyran-merocyanine transition is occurring for the derivatized contrast agent. The relaxivity for the complexes in solution is determined after intense UV irradiation (to convert to the merocyanine form) or visible irradiation (to convert to spiropyran). Relaxivity can be measured using a relaxometer (Bruker Minispec). The agent also can be characterized by electrochemistry to ascertain its redox properties and evaluate its suitability for membrane studies. Zhi, J., Baba, R., Hashimoto, K. & Fujishima, A. (1995) *J. Photochem. Photobio. A: Chem* 92, 91–97.

Relaxivity of the contrast agent also can be determined in the presence of liposomes, a model membrane system, to investigate whether membrane-localization significantly affects contrast enhancement. Liposomes are generated using standard techniques by probe sonication of a buffered solution of phosphatidylcholine (PC, 25 mM). Operative compounds of the invention localize to the liposomes. If the difference in relaxivity between UV and visible light irradiated contrast agent is unchanged in the presence of membrane, this indicate that there is little modification of the water environment about the compound when it is membrane localized. Conversely, a change in the behavior of the contrast agent in the presence of liposomes compared to results in liposome-free solution indicates that difference in water interaction for membrane associated agent is significant. These data provide interesting insight to the closeness of association of the spiropyran-derivatized contrast agent with the membrane. Longer linkers place the lanthanide chelator farther from the membrane and minimize the contribution from the membrane localization mechanism.

The contrast agents' responses to membrane potentials also can be tested in the liposome system. Membrane potentials can be induced in unilamellar phosphatidylcholine (PC) vesicles having preformed KCl gradients by the addition of valinomycin (20 mg/mmole PC). Cabrini, G. & Verkman, A. (1986) *J. Membrane Biol.* 92, 171–182; Plasek, J. & Sigler, K. (1996) *J. Photochem. Photobio.* 33, 101–124. Relaxivity of water is determined in vesicle suspensions before and after the addition of valinomycin. For well-behaved contrast agents, values correlate with those obtained by light-induced isomerization of the contrast agent. The valinomycin assay is a "one-way" experiment in which the response of the contrast agent to hyperpolarization can be measured, but reversal to resting state cannot. To demonstrate reversibility, a cellular assay is used, as described below.

The response of the contrast agents to membrane potentials as opposed to light can be assessed in cultured cells. Cultured cardiac cells with contractile activity (e.g. HL-1) (or any other spontaneously active electrically-excitable cell such as cultured pacemaker neurons) are well suited for assaying the contrast agents of the invention. The cells are incubated with (or without, as a control) the contrast agents and observed by light microscopy. When incubated with operative contrast agents of the invention, the beating of the cells produces a corresponding pattern of absorbance changes in the membrane and extracellular space. Short exposure images are obtained from the cells and the correlation established by analysis of the captured images. These cells also can be examined by MRI microscopy. Acquisition parameters are set to capture images down to hundreds of microseconds and are adjusted to best reflect the periodic change in membrane potential that will vary as a function of the particular cell type and culture condition.

When cardiac myocytes are used for the assay, pharmacologic agents can be used to further evaluate the ability of the contrast agent to accurately reflect changes in membrane activity. For example, the cells can be imaged in the presence of a modulator of cardiac activity such as isoproterenol, which perturbs the synchrony of cardiomyocyte contractile activity, or phenylephrine, which increases contractile activity. Jahangiri, A., Leifert, W., Patten, G. & McMurchie, E. (2000) *Mol. Cell. Biochem.* 206, 33–41; McWhinney, C., Hansen, C. & Robishaw, J. (2000) *Mol. Cell. Biochem.* 214, 111–119. Cells are grown in culture and incubated with the contrast agent±modulator, imaged using one or more of the techniques described above (i.e., light or MRI microscopy) and the data are analyzed to determine whether the modulator's expected effect is reflected in the signal generated by the assayed contrast agent. Whole dishes of cells can be imaged by MRI. Alternatively, cells can be grown in a three-dimensional matrix and imaged as such. Cardiomyocytes can be grown as clusters in a three-dimensional cell culture system. Igelmund, P., Fischer, I., Soest, J., Gryschenko, O., Fleichmann, B. & Hescheler, J. (1997) *Pflugers Archiv-Eur J Physiol* 433, P293—P293 Suppl. S. A number of other three-dimensional culture systems have been reported in which normally monolayer cells are grown in matrices of denatured collagen or microporous carriers. Bancel, S. & Hu, W. (1996) *Biotech Progress* 12, 398–402; Heermeier, K., Spanner, M., Trager, J., Gradinger, R. & Schmidt, J. (1995) *Cells and Materials* 5, 309–320. Diffusivity of the contrast agents of the invention through cells in three-dimensional culture provides a proxy for the ability of the agents to diffuse throughout tissues in vivo.

Example 5

Determining the Pharmacokinetics and Biodistribution of Compounds of the Invention In vivo tissue distribution of the compounds of the invention can be assessed in mouse and rat models using a radiolabeled derivative of the contrast agent. $^{111}$Indium is substituted for the lanthanide (preferably gadolinium) in the synthesis of the agent. $^{111}$Indium is routinely used as a radioactive substitute for gadolinium and is a gamma emitter. Duncan, J. R., Franano, F. N., Edwards, W. B. & Welch, M. J. (1994) *Inves. Radiol.* 29, S58–S61; Jasanada, F., Urizzi, P., Souchard, J., Gaillard, F. L., Favre, G. & Nepveu, F. (1996) *Bioconj. Chem.* 7, 72–81. $^{111}$Indium is employed because it has a half-life of 2.8 days compared to 242 days for $^{153}$Gd and has emissions about twice as energetic. A radiolabeled contrast agent of the present invention is introduced into the animal and whole body distribution is assessed at various time points after administration. A number of techniques can be used to introduce the agent to the animal including by way of example but not limitation: intravenous, intraperitoneal, intravitreal and subretinal. Key organs and tissues are harvested and gamma counted. Blood samples are taken and counted over time to determine blood clearance rates. Systemic (I.V, I.P), intravitreal and subretinal delivery methods can be used to assess distribution of compounds of the invention to the eye, particularly the retina.

Example 6

Use of Compounds of the Invention in an Animal Model of Retinal Degeneration An animal model is used to demonstrate the ability of a contrast agent of the present invention to produce an image of retinal activity and detect photoreceptor loss in a mouse or rat model of human retinal degeneration disease. A number of animal models of retinal degeneration are available and useful for this purpose. For example, the B6.BR-pcd strain of mice suffers from a Purkinje cell defect which results in complete photoreceptor degradation in the course of one year; SAM mice experience profound loss of photoreceptors in the peripheral retina; a number of rd mutant mice are models for retinal degeneration and retinitis pigmentosa (rd6 mice show abnormal ERG at 1–2 months); and Fischer 344 rats show age-related retinal degeneration. DiLoreto, D., Martzen, M., delCerro, C., Coleman, P. & delCerro, M. (1995) *Brain Res.* 698, 1–4; Shoji, M., Okada, M., Ohta, A., Higuchi, K., Hosokawa, M. & Honda, Y. (1998) *Ophthalmic Res* 30, 172–179; Porteracailliau, C., Sung, C., Nathans, J. & Adler, R. (1994) *PNAS* 91, 974–978; Eversole-Cire, P., Conception, F., Simon, M., Takayama, S., Reed, J. & Chen, J. (2000) *Inv. Opth. Vis. Sci.* 41, 1953–1961; Hawes, N., Chang, B., Hageman, G., Nusinowitz, S., Nishina, P., Schneider, B., Smith, R., Roderick, T., Davisson, M. & Heckenlively, J. (2000) *Inv. Opth. Vis. Sci.* 41, 3149–3157. Using the most efficient injection method, as determined from the biodistribution studies described in Example 5, contrast agent is introduced to mouse or rat eyes. Animals under even illumination by wavelengths of light that do not trigger the indicator group conformational change are MR imaged in small animal probes using RF surface coils designed for imaging the eye to generate high resolution MRI images of the retina. The animals are imaged over time as the retina progressively deteriorates. At various time points, animals are sacrificed and the retinas prepared for histological confirmation of photoreceptor degradation and optionally, 2-D electroretinography (2D-ERG). The MRI results are correlated with the histological results and optionally with those from 2D-ERG.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A compound, comprising:
   an indicator moiety capable of adopting at least two conformations, wherein the equilibrium between said at least two conformations is altered by a membrane potential, wherein said indicator moiety is selected from the group consisting of a spiropyran, a merocyanine, a cyanine, and an indoline;
   a DO3A bound to said indicator moiety;
   and a lanthanide chelated within said DO3A, wherein the interaction of said chelated lanthanide with a solvent is altered by a change in the equilibrium between said at least two conformers of said indicator moiety.

2. The compound of claim 1, wherein said solvent is water.

3. The compound of claim 1, wherein said DO3A is bound to said indicator moiety through a linker.

4. The compound of claim 1, wherein said indicator moiety is a spiropyran.

5. The compound of claim 4, wherein said spiropyran is spirobenzopyran.

6. The compound of claim 4, wherein said spiropyran is spirobenzothiopyran.

7. The compound of claim 1, wherein said lanthanide is gadolinium.

8. The compound of claim 1, comprising the formula:

wherein $R_1$ is selected from the group consisting of $C_nH_{2n+2}$, $C_nH_{2n}$, and a combination of both and wherein n is 0 to 4, inclusive;
wherein each of $R_2$–$R_7$ is independently selected from the group consisting of H, $CH_3$, phenyl, and a bulky steric-hindering group;
and wherein $A^-$ is independently selected from $COO^-$, $PO_3^{2-}$, and another lanthanide—coordinating group.

9. The compound of claim 8, wherein $R_1$ is $CH_2$, $R_2$–$R_7$ each is H, and $A^-$ is $COO^-$.

10. The compound of claim 8, wherein said La is Gd.

11. A composition, comprising the compound of claim 1 and a pharmaceutically acceptable excipient.

12. A composition, comprising the compound of claim 4 and a pharmaceutically acceptable excipient.

13. A composition, comprising the compound of claim 7 and a pharmaceutically acceptable excipient.

14. A composition, comprising the compound of claim 8 and a pharmaceutically acceptable excipient.

15. A composition, comprising the compound of claim 9 and a pharmaceutically acceptable excipient.

16. A composition, comprising the compound of claim 10 and a pharmaceutically acceptable excipient.

17. A method of generating a magnetic resonance image of a membrane potential, comprising:
    contacting a cell with the compound of claim 1; and
    generating a magnetic resonance image of said cell, wherein said magnetic resonance image provides information about the membrane potential of said cell.

18. A method of generating a magnetic resonance image of a membrane potential, comprising:
    contacting a cell with a compound of claim 8; and
    generating a magnetic resonance image of said cell, wherein said magnetic resonance image provides information about the membrane potential of said cell.

19. A method of testing a compound for suitability as a magnetic resonance imaging probe of membrane potential, comprising:
    contacting an electrically-excitable cultured cell with a compound of claim 1;
    generating a magnetic resonance image of said cell; and
    determining whether said magnetic resonance image provides information about the membrane potential of said electrically excitable cell.

20. The method of claim 19, wherein said electrically excitable cell is selected from the group consisting of a neuron and a muscle.

21. The method of claim 19, wherein said electrically excitable cell is a cardiac muscle cell.

22. The method of claim 19, wherein said culture is a three-dimensional culture.

23. A method of testing a compound for suitability as a magnetic resonance imaging probe of membrane potential, comprising:
    contacting an electrically-excitable cultured cell with a compound of claim 8;
    generating a magnetic resonance image of said cell; and
    determining whether said magnetic resonance image provides information about the membrane potential of said electrically excitable cell.

24. The method of claim 23, wherein said electrically excitable cell is selected from the group consisting of a neuron and a muscle.

25. The method of claim 23, wherein said electrically excitable cell is a cardiac muscle cell.

26. The method of claim 23, wherein said culture is a three-dimensional culture.

27. The compound of claim 8 wherein $R_1$ is $CH_2$, $R_2$–$R_7$ each is H, A– is $PO_3^{2-}$, and La is Gd.

* * * * *